(12) United States Patent
Li et al.

(10) Patent No.: US 6,610,079 B1
(45) Date of Patent: Aug. 26, 2003

(54) FIXATION SYSTEM AND METHOD

(75) Inventors: Lehmann K. Li, Milford, CT (US); Rhodemann Li, Darien, CT (US)

(73) Assignee: Linvatec Corporation, Largo, FL (US)

( * ) Notice: Subject to any disclaimer, the term of this patent is extended or adjusted under 35 U.S.C. 154(b) by 213 days.

(21) Appl. No.: 09/610,123

(22) Filed: Jun. 30, 2000

Related U.S. Application Data (60) Provisional application No. 60/170,714, filed on Dec. 14, 1999, provisional application No. 60/175,804, filed on Jan. 12, 2000, and provisional application No. 60/202,092, filed on May 4, 2000.

(51) Int. Cl.⁷ .............................................. A61B 17/04
(52) U.S. Cl. ........................ 606/232; 606/76; 606/213; 606/228
(58) Field of Search ........................... 606/72, 75, 213, 606/216, 74, 153, 155

(56) References Cited

U.S. PATENT DOCUMENTS

| | | | |
|---|---|---|---|
| 4,063,582 A | 12/1977 | Fischer | |
| 4,065,817 A | 1/1978 | Branemark et al. | |
| 4,274,163 A | 6/1981 | Malcom et al. | |
| 4,494,535 A | 1/1985 | Haig | |
| 4,514,125 A | 4/1985 | Stol | |
| 4,554,686 A | 11/1985 | Baker | |
| 4,625,722 A | 12/1986 | Murray | |
| 4,653,487 A | 3/1987 | Maale | |
| 4,712,957 A | 12/1987 | Edwards et al. | |
| 4,851,005 A | 7/1989 | Hunt et al. | |
| 5,013,316 A | 5/1991 | Goble et al. | 606/232 |
| 5,167,665 A | 12/1992 | McKinney | |
| 5,192,282 A | 3/1993 | Draenert | |
| RE34,293 E | 6/1993 | Goble et al. | 606/232 |
| 5,268,001 A | 12/1993 | Nicholson et al. | 606/232 |
| 5,269,783 A | 12/1993 | Sander | |
| 5,501,687 A | 3/1996 | Willert et al. | |
| 5,501,695 A | 3/1996 | Anspach, Jr. et al. | 606/232 |
| 5,514,137 A | 5/1996 | Coutts | |
| 5,593,425 A | 1/1997 | Bonutti et al. | 606/232 |
| 5,597,383 A | 1/1997 | Carbone | |
| 5,624,462 A | 4/1997 | Bonutti | 606/232 |
| 5,643,319 A | 7/1997 | Green et al. | |
| 5,645,589 A | 7/1997 | Li | 606/232 |
| 5,665,110 A | 9/1997 | Chervitz et al. | |
| 5,725,529 A | 3/1998 | Nicholson et al. | 606/232 |
| 5,725,541 A | 3/1998 | Anspach, III et al. | 606/232 |
| 5,741,282 A | 4/1998 | Anspach, III et al. | 606/232 |
| 5,766,250 A | 6/1998 | Chervitz et al. | |
| 5,895,425 A | 4/1999 | Grafton et al. | |
| 5,911,721 A | 6/1999 | Nicholson et al. | 606/232 |

(List continued on next page.)

FOREIGN PATENT DOCUMENTS

| | | |
|---|---|---|
| DE | 2529699 | 3/1976 |
| DE | 3841704 | 6/1990 |
| DE | 19545612 | 6/1997 |
| DE | 29914192 | 11/1999 |
| EP | 0376641 | 7/1990 |
| EP | 0464479 | 1/1992 |

(List continued on next page.)

OTHER PUBLICATIONS

JP 6–169944 A., In: Patent Abstracts of Japan, C–1251, Sep. 20, 1994, vol. 18, No. 501.

*Primary Examiner*—Gary Jackson
(74) *Attorney, Agent, or Firm*—Ostrolenk, Faber, Gerb & Soffen, LLP (57) ABSTRACT

A fastener system and procedure to secure a member in a medium. The system includes a tool to deliver both the member and a flowable, curable polymer onto, into or through the medium. The flowable polymer is injected into, through or around the member. As the flowable polymer cures, it acts as either a solid filler or as an adhesive to provide fixation for the member, or to enhance fixation of the member.

110 Claims, 9 Drawing Sheets

U.S. PATENT DOCUMENTS

| | | | |
|---|---|---|---|
| 5,928,267 A | 7/1999 | Bonutti et al. | 606/232 |
| 5,941,901 A | 8/1999 | Egan | |
| 5,961,521 A | 10/1999 | Roger | |
| 5,968,044 A | 10/1999 | Nicholson et al. | 606/232 |
| 5,976,127 A | 11/1999 | Lax | |
| 5,980,524 A | 11/1999 | Justin et al. | |
| 5,980,559 A | 11/1999 | Bonutti | 606/232 |
| 5,989,282 A | 11/1999 | Bonutti | 606/232 |
| 6,007,567 A | 12/1999 | Bonutti | |
| 6,022,373 A | 2/2000 | Li | 606/232 |

FOREIGN PATENT DOCUMENTS

| | | |
|---|---|---|
| EP | 0496140 | 7/1992 |
| EP | 0504915 | 9/1992 |
| EP | 0611557 | 8/1994 |
| EP | 0700671 | 3/1996 |
| EP | 0747023 | 12/1996 |
| EP | 0995409 | 4/2000 |
| GB | 2307179 | 5/1997 |
| GB | 2312376 | 10/1997 |
| WO | 9830141 | 7/1998 |
| WO | 9901084 | 1/1999 |

FIXATION SYSTEM AND METHOD

CROSS REFERENCE TO RELATED APPLICATIONS

This application claims the priority and benefit of U.S. Provisional patent applications 60/170,714 filed Dec. 14, 1999, 60/175,804 filed Jan. 12, 2000 and 60/2202,092, filed May 4, 2000 and entitled, respectively, INJECTABLE RIVET FASTENER APPARATUS AND METHOD, INJECTABLE RIVET FASTENER APPARATUS AND METHOD and FASTENER APPARATUS (POLYMER ANCHOR) AND METHOD AND METHOD FOR MIXING AND DELIVERING TWO COMPONENT CEMENT/POLYMER

BACKGROUND OF THE INVENTION

The present invention relates to anchoring devices and methods and, in particular, to anchors for securement in first members and which allow attachment of second members to the first members. The invention accordingly relates to devices for coupling a second member, e.g., a cylindrical or tubular member, or a fastener, to a first member.

There is a need for a simple acting and quickly installable device for coupling a second member to a first member. There is particularly a need for such a device in the medical and surgical fields. In particular, there is a need for such a device that can be used to connect tissues or bones to other tissues or bones. Furthermore, there is a need for a device which will allow manmade materials to be connected to tissue or bones, in particular, to allow cylindrical or rod shaped objects, e.g., prostheses, to be fastened to a bore in a bone or other tissue. There is furthermore a need for an easily installable device for anchoring or fastening sutures to tissue, which sutures may then be connected to another object, for example, other tissue.

In the medical and surgical fields, there is a particular need for a device that can be coupled to a first object that is then inserted into a second object, thereby to quickly lock the first and second objects together. For example, there is a need for such a device that can connect prostheses to bone, or bone to bone. There is furthermore a need for such a connection device that is essentially hollow in the interior thereby to allow placement of parts of tissue, bone or manmade materials inside the device, such as rods, pins, sutures, valves, adhesives, flowable polymers, gels, etc.

There is also a need for a device that can lock two objects together in a quick and simple manner, for example, by compression, thereby to lock a component inside the device and simultaneously to a medium, for example, bone. There is a need for such a device for locking two components together, for example, bone and bone or tissue and bone or tissue and tissue, and which device can be left hollow to allow fluid to pass through the inserted device. There is furthermore a need for such a device that can direct or inhibit the flow of fluid passing through the device. Such a device could be used in the medical field to connect bone to bone, for example, to repair fractures or in spinal surgery. Such a device could also be used to connect other materials to bone, for example, prostheses to bone. These could be used in hip prostheses, knee prostheses or as bone plugs and dental implants.

There is furthermore a need for such a connection device that allows connection of tissue to bone. This could be used for ligament repair, meniscus repair and soft tissue repair. There is also a need for such a device that can provide tissue to tissue connections, for example, liver, lung and spleen resections.

There is also a need for such a device that allows materials to be connected to tissue, or tissue to tissue. Such a device could be used to repair tears in soft tissue that may not have avulsed from bone, such as meniscal tears, or for wound closure.

Various anchoring devices and devices for securement in tissue are known. For example, in U.S. Pat. No. 5,514,137 to Coutts, an implant is fastened in a bore by applying an effective amount of resorbable cement such that temporary fixation occurs until permanent fixation occurs by osteogenic growth between the bone and part of the implant. In U.S. Pat. No. 5,192,282, to Draenert, a screw is fastened in a bore in an essentially vacuum-tight manner and a substance is delivered into bone through a longitudinal communication channel in the screw. In U.S. Pat. No. 4,712,957, to Edwards, a fastener is secured by introducing a fluent adhesive into longitudinal channels formed along the shank of the fastener. In U.S. Pat. No. 5,665,110 to Chervitz, et al., a suture is anchored into a hole created in bone by filling the hole containing a suture with an adhesive material. In U.S. Pat. No. 5,702,446 to Shenck, a prosthesis is affixed in bone by utilizing a port hole in the prosthesis to introduce fluid into an internal chamber that is connected to the porous mesh bone-mating surface. In U.S. Pat. No. 4,653,489 to Tronzo, a hip screw fixation is enhanced through the delivery of cement to a through-bore in the screw having longitudinally spaced fenestrations in one side. In U.S. Pat. No, 4,494,535 to Haas, a cannulated hip fixation nail has a plurality of ports located in flanges that are separated by fluted areas to receive a cement. In. U.S. Pat. No. 4,653,487 to Maale, a cannulated intramedullary rod has circumferentially spaced threaded apertures to allow cement to discharge into adjacent bone tissue.

In each of the above patents, a flowable material is used in conjunction with a device to provide fixation or to enhance fixation of a device in tissue.

In another patent, U.S. Pat. No. 5,643,319 to Green, a surgical instrument is used to apply a fastener with two legs joined by a flexible material. This instrument and fastener system does not use a flowable material.

None of these patents, however, provides for a convenient means to quickly and securely anchor at least one member in at least one medium by using a single tool to deliver both the member and the flowable, curable material.

SUMMARY OF THE INVENTION

It is an object of the present invention to provide an anchoring device for securement in a medium.

It is also an object of the present invention to provide a connection device for connecting a first object to a second object and, particularly such a connection device that is simple to use and quick acting.

It is yet a further object of the present invention to provide such a connection device that is suitable for the medical and surgical fields.

It is yet still a further object of the present invention to provide such a device that is suitable for use with bone, tissue or foreign objects, for example, prosthetic devices or any combinations thereof.

The above and other objects of the present invention are achieved by an installation tool, for the placement of both a member and a flowable material into a medium. The tool comprises a hollow distal longitudinal section with at least a portion in contact with at least a portion of the member. The longitudinal distal section of the tool is capable of both controlling the member and delivering the flowable material into the medium. The distal longitudinal section of the tool is connected to a proximal handle that serves for inserting the member and injecting the flowable material into the medium.

The objects of the present invention are also achieved by a method for using an installation tool for the placement of both a member and a flowable material into a medium. The method comprises using an installation tool with a hollow distal longitudinal section with at least a portion in contact with at least a portion of the member. The longitudinal distal section of the tool is capable of both controlling the member and delivering the flowable material into the medium. The distal longitudinal section of the tool is connected to a proximal handle that serves for both inserting the member and injecting a flowable material into the medium.

Another object of the present invention is to provide an installation tool that can insert a member by applying rotational force, such as for example, a threaded member, and deliver a flowable material into a medium.

Yet another object of the present invention is to provide an installation tool that can insert a member by applying an axial force, such as for example, a wire, anchor, staple, rod, tube, suture, etc., and deliver a flowable material into a medium.

Still a further object of the present invention is to provide an installation tool that can insert a member by applying an impacting force, such as for example, a tack, nail, pin, etc., and deliver a flowable material into a medium.

Another object of the present invention is to provide an installation tool that can insert a member and deliver a flowable material in a bore in a medium.

Another object of the present invention is to provide an installation tool that can insert and maintain the position of a member in a medium while the distal most section of the tool is being withdrawn, for example, to deliver the flowable material in a distal to proximal direction.

Yet another object of the present invention is to provide an installation tool that can deliver the flowable material and then insert a member in a medium.

An additional object of the present invention is to provide a member that may be cannulated at least partially to receive either the distal section of the tool or the flowable material, or both. Furthermore, the member may have at least one side channel or port connected to the through-bore to allow the flowable material to engage with the surrounding medium.

Yet another object of the present invention is to provide a member that may have fluted sides to allow the flowable material to engage with the medium.

A further object of the present invention is to provide a member that may be a flexible element, such as a suture, at least a portion of which the flowable material may surround.

Still another object of the present invention is to provide a member that may have more than one component, at least one of which may be a flexible element, such as a staple with a suture bridge.

It is yet still a further object of the present invention to provide a fixation method and apparatus using a flowable material that is resorbable, remodelable, or permanent.

Another object of the present invention is to provide a fixation method and apparatus employing a flowable material whose curing may be reversed to allow for its removal.

A further object of the present invention is to provide a fixation method and apparatus employing a flowable material that cures in an appropriate time period for a particular application, e.g., a short time for certain sports medicine applications, and a longer time for general orthopaedic applications.

Still a further object of the present invention is to provide a fixation method and apparatus employing a flowable material that cures, hardens, becomes a solid or gel, adheres, crosslinks, polymerizes, or otherwise no longer flows.

Still another object of the present invention is to provide a fixation method and apparatus employing a flowable material that can be injected, sprayed, poured, or otherwise delivered through a cannulated section of an installation tool.

It is still a further object of the present invention to provide a method to use an installation tool to insert a member and deliver a flowable material in a medium for orthopaedic applications.

It is also an object of the present invention to provide a method to use an installation tool to insert a member and deliver a flowable material in a medium for any surgery applications in general, such as soft tissue to soft tissue apposition.

Other features and advantages of the present invention will become apparent from the following description of the invention that refers to the accompanying drawings.

BRIEF DESCRIPTION OF THE DRAWINGS

The invention will now be described in greater detail in the following detailed description with reference to the drawings in which.

DETAILED DESCRIPTION OF EMBODIMENTS OF THE INVENTION

Figure 1A:
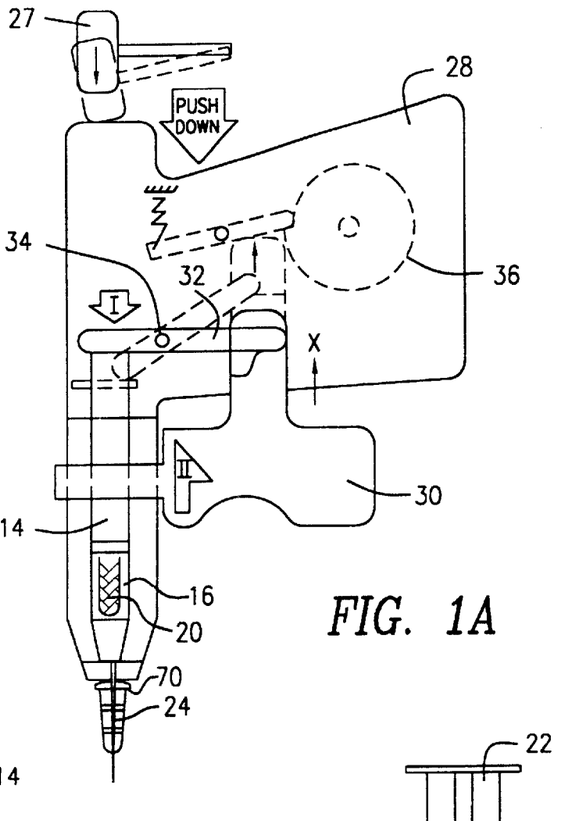
FIG. 1A is a side view showing a preferred embodiment of an installation tool of the present invention with a fastener member releasably attached.
Figure 1B:
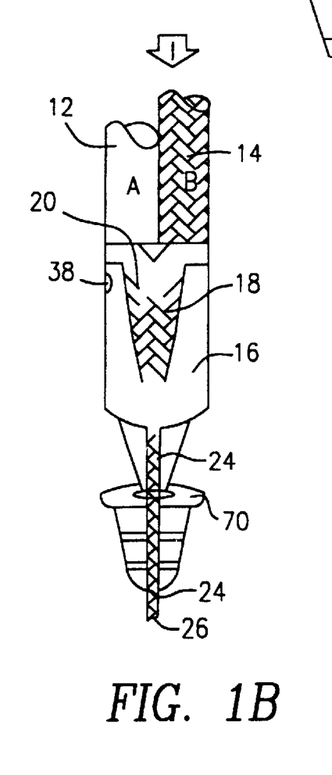
FIG. 1B is a side view of the distal end of the invention of FIG. 1A.
Figure 1C:
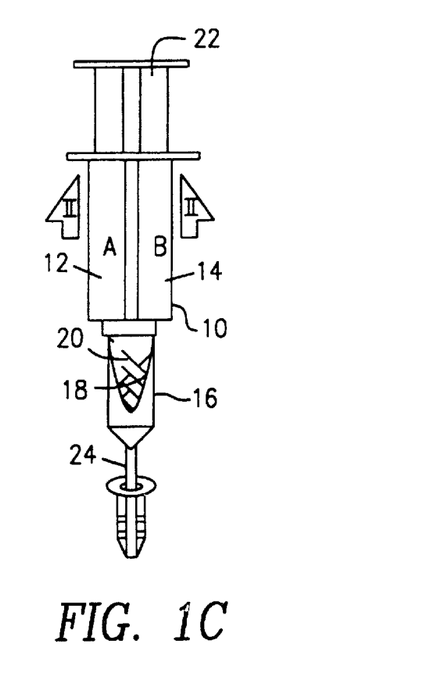
FIG. 1C is a side view of the distal end of the invention of FIG. 1A during the delivery of the flowable material.

With reference now to the drawings, FIGS. 1A, 1B and 1C show a first embodiment of an installation tool according to the invention.

As shown in FIGS. 1A, 1B and 1C, one embodiment of the installation tool comprise a double barrelled syringe 10 comprising two chambers 12 and 14. Each chamber is adapted to receive at least one component of a preferably two component polymer. The components need not both be fluids. For example, one or both could be a powder or particulate. One or more of the components may comprise a fluid containing a particulate. The individual components A and B are located prior to mixing in the chambers 12 and 14, and when mixed, form a curable or hardenable polymer or cement. Chambers 12 and 14 each feed into a prechamber 16 which includes a stationary mixing chamber 18 having a plurality of mixing baffles as shown at 20 in FIG. 1B. The two components identified as A and B are forced by the double plunger 22 into the stationary mixing chamber 18 where they are mixed and dispensed into the chamber 16. Once in chamber 16, the polymer has been mixed so that the hardening process will begin after a period of time elapses. The chamber 16 leads to the syringe needle 24, which dispenses the properly mixed polymer through a distal opening 26.

Although a two component system is shown in FIG. 1A, a single component system, having only one chamber, is also within the scope of the invention.

As shown in FIG. 1A, the installation tool further comprises a handle 28 having a trigger 30 attached thereto. The trigger 30 is coupled to a lever 32 pivoting about an axis 34. When the trigger 30 is depressed so that it moves in the direction of arrow X of FIG. IA, the lever 32 pivots counterclockwise forcing the syringe plungers 22 into the chambers 12 and 14, causing the two components to be dispensed into the mixing chamber 18.

In accordance with the invention, a timer can be provided as indicated schematically at 36. Once the trigger has been depressed and the plungers have been fully actuated, and after the needle 24 has been pulled upwardly in accordance with the desired distribution of the polymer in the medium (described in greater detail below) the timer is activated. The timer can give a tactile or audible feedback indicating that the polymer components have been properly dispensed and cured.

In accordance with the invention, the installation tool may be a single use tool or a reuseable tool. With a single use tool, the two components A and B may be supplied in the syringe barrels with the tool for this single use. If reuseable, the components A and B can be loaded into the chambers 12 and 14 after each use. It may be necessary to make the chamber 16, mixing chamber 18 and needle 24 removable so they can be cleaned or, just the portion comprising the mixing chamber 18, chamber 16 and needle 24 may be needed to be replaced prior to each use. Preferably, however, the tool is a single use tool, with the polymer components already supplied in the barrels prior to use.

To employ the device according to the present invention, the trigger is depressed causing the two components A and B to be delivered into the mixing chamber 18. This can be done prior to, during or after insertion of the needle 24 into the tissue. The needle 24 can have attached thereto a suture, as shown in greater detail in FIG. 7 The needle 24 may be specially adapted to allow securement of a suture thereto, as will be explained later. Alternatively, the needle 24 has disposed around it a non-flowable implant or fastener such as the fastener 70 of FIG. 1A. The fastener 70 with needle disposed therearound is inserted into the tissue as a unit. The fastener 70 may be held temporarily by a holding device at the distal portion of the tool or merely held in place by its disposition around the needle 24. The mixing of the components A and B may be started prior to the insertion of the needle (or needle and fastener) into the tissue, during insertion of the needle (needle and fastener) into the tissue or after the needle (needle and fastener) has been inserted into the tissue. Once the needle has been inserted into the tissue and the mixed polymer is being delivered to the tip of the needle and entering into the hole in the tissue surrounding the needle, the needle is preferably moved upwardly, thereby allowing the mixed polymer to be distributed evenly or in a desired pattern into the tissue. This will be described in greater detail with reference to FIG. 6.

As shown in FIG. 1B, it may be necessary to provide an air vent 38 to allow any not yet fully mixed polymer in chamber 16 to be housed in the chamber 16 so the not yet fully mixed polymer will not get into the tissue. The chamber 16 is provided to capture the first portion of the polymer which is not yet fully mixed. It allows for properly mixing the polymer and for the properly mixed polymer to be forced through the needle into the tissue prior to fully curing.

As also shown in FIG. 1A, an axial force, such as a tapping force provided by a mallet 27, may be employed to insert the non-flowable implant 70.

Figure 2:
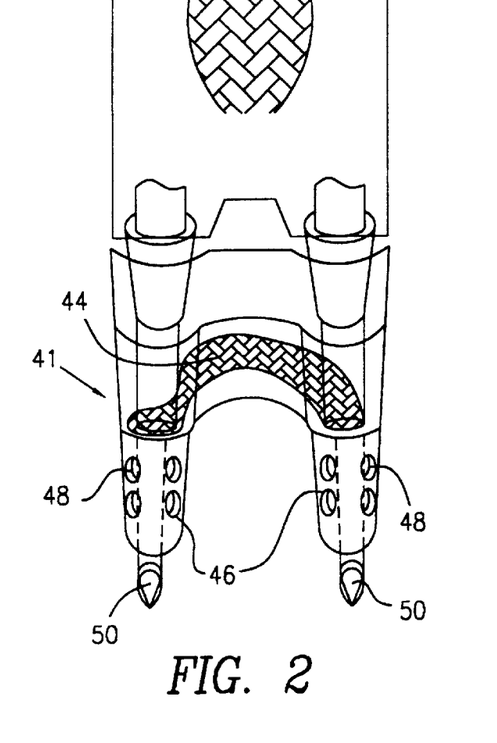
FIG. 2 is a close up view of the distal end of the invention of FIG. 1, showing a preferred embodiment of a member releasably attached to the tool.
Figure 3:
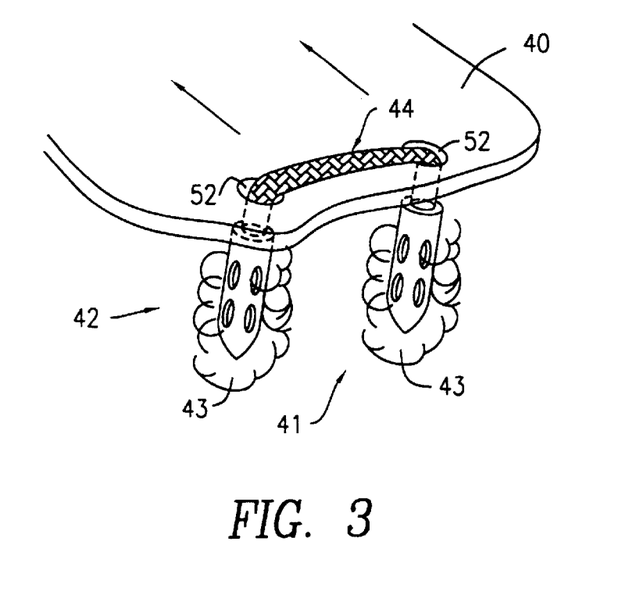
FIG. 3 shows the invention of FIG. 2, the member having been inserted in a medium and a flowable material delivered through the member and into the medium.
Figure 3A:
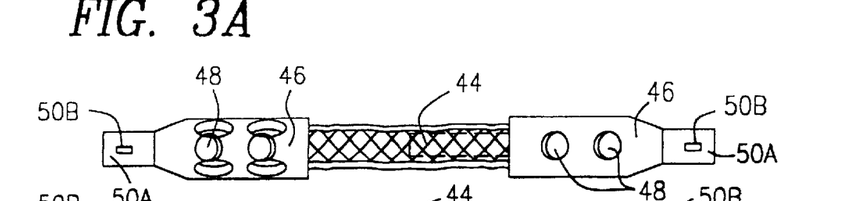
FIGS. 3A and 3B show, respectively, one method to manufacture the embodiment of FIG. 2 in a top view, and in a side view.

FIG. 2 shows a staple design which can allow the securement of, for example, soft tissue 40 to, for example, other tissue, for example, bone, shown schematically at 42 in FIG. 3. Another embodiment of this staple is shown in FIGS. 3A and B in an unfolded top view and a side view.

As shown in FIG. 2, the staple 41 comprises a ribbon or suture 44 which is coupled to sleeves 46 which may be biodegradable, bioabsorbable, remodelable or permanent. Any component of the staple 41 and any other fastener disclosed herein may be biodegradable, bioabsorbable, remodelable (capable of conversion into tissue or inducing growth of tissue) or permanent. The sleeves have openings 48 therein. At the distal ends of the sleeves 46, piercing elements 50 may be disposed. The piercing elements 50 can be, for example, the distal tips of the needles 24 of the installation tool shown in FIGS. 1A to 1C. The staple, generally indicated by the reference numeral 41, is inserted through the tissue 40. See FIG. 3. The piercing elements 50 will form holes 52 in the tissue 40 (See FIG. 3). The staple may be inserted into either predrilled holes in the bone 42 or forms its own holes in the bone tissue 42 either by tapping or compression by using a tool which forces the piercing members 50 into the tissue 42. Once the suture 44 has sufficient tension to hole tissue 40 to tissue 42, the tool, which is like the tool shown in FIG. 1 but having two needles 24 for dispensing the mixed polymer into both biodegradable sleeves 46, is activated to force the mixed polymer into the biodegradable sleeves 46. The mixed polymer is dispensed through the openings 48 so that it enters into the tissue. Once it is cured, the tissue 40 has been secured to the bone or other tissue 42 by the action of the cured polymer 43 securing the sleeves 46 into the bores 52

(i addition to any other mechanical or frictional engagement provided by the fastener itself). The sleeves 46 are preferably biodegradable, so that they will biodegrade after time, allowing new tissue growth to secure the tissue 40 to the tissue 42. As discussed, to secure the desired distribution of polymer 43, the needles 24A may be moved upwardly in sleeves 46 as the polymer is injected.

Figure 7A:
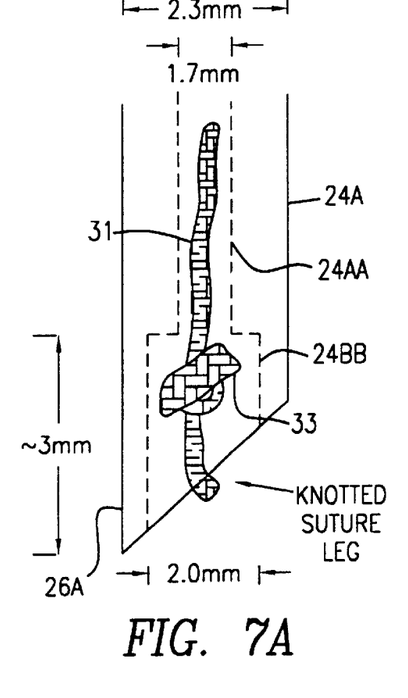
FIGS. 7A and 7B show distal ends of a modified form of the tool of FIG. 1 useful for anchoring a suture, in respectively, a side view and cross sectional view.
Figure 7B:
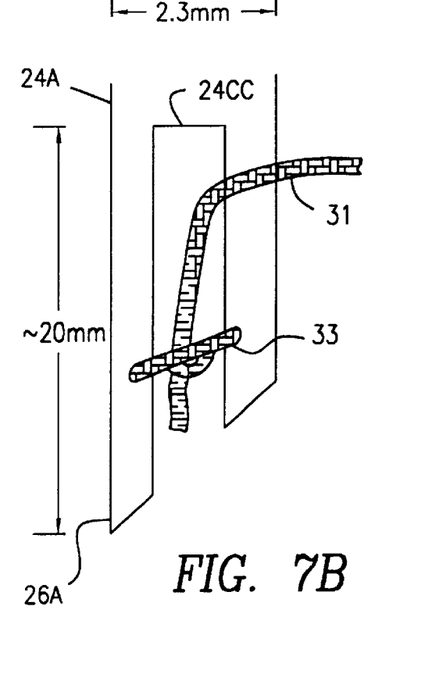
Figure 7C:
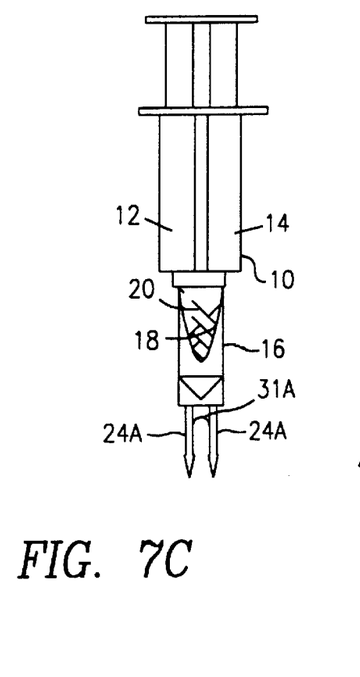
FIG. 7C shows the device of FIGS. 1A, 1B and 1C modified to deliver a suture staple and having needle distal ends in accordance with FIGS. 7A and 7B.
Figure 7D:
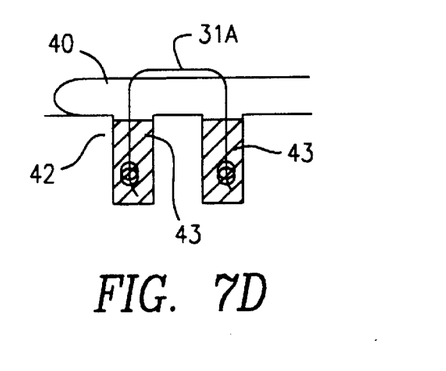
FIG. 7D shows an installed suture staple.

A modified form of the installation tool of FIG. 1 having two needles with side slots for sutures as shown in FIGS. 7A and 7B and having a suture extending between the needles as shown in FIG. 7C (described in detail later), can be used as a staple insertion tool. In such case, the sleeves 46 and metallic inserts 50 need not be employed. The surgeon inserts both needles simultaneously into the tissue, obtains the required tension on the suture and then injects the mixed polymer into each of the needles simultaneously, thus securing the end of each suture and preferably the knot of each suture to the tissue. Preferably, upon curing, the needles are removed, leaving the secured suture stapled to the tissue. Alternatively, the needles may be removed prior to curing. An installed example of this suture staple is shown in FIG. 7D.

Figure 3B:
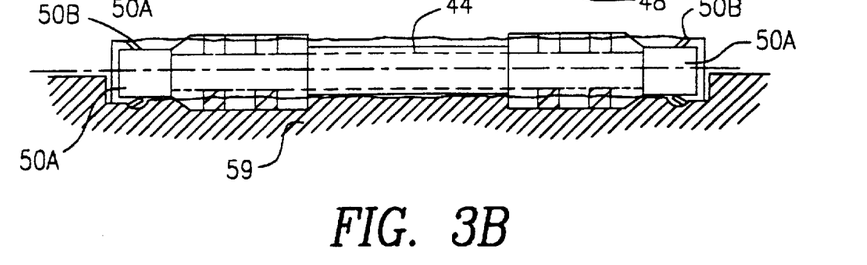

FIG. 3A shows a method to manufacture the staple of FIG. 3 in a laid out top view. FIG. 3B shows the staple in a side view. In order to attach suture 44 to the sleeves 46, an insert molding technique can be used. The insert mold is shown at 59. According to this technique, which is not exclusive, the suture 44 is deposited or inserted into the mold and the sleeves 46 are thereafter molded to the suture 44. Reference items 50A are hold down members used during the molding process to secure the suture 44 to the mold. Suture hooks 50B are used to secure the suture 44 to the hold down members.

Figure 4:
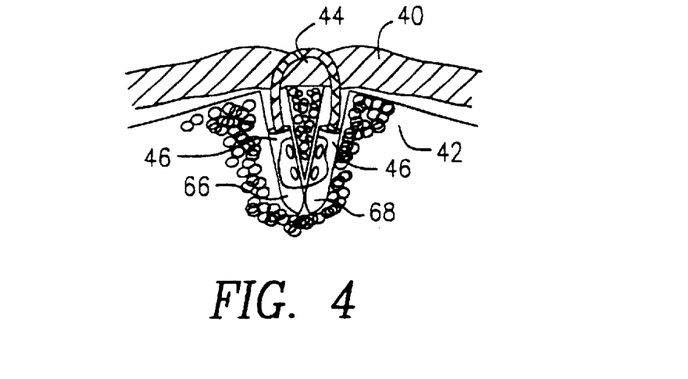
FIG. 4 is a side view of the member of FIG. 2 inserted into a hard medium.
Figure 4A:
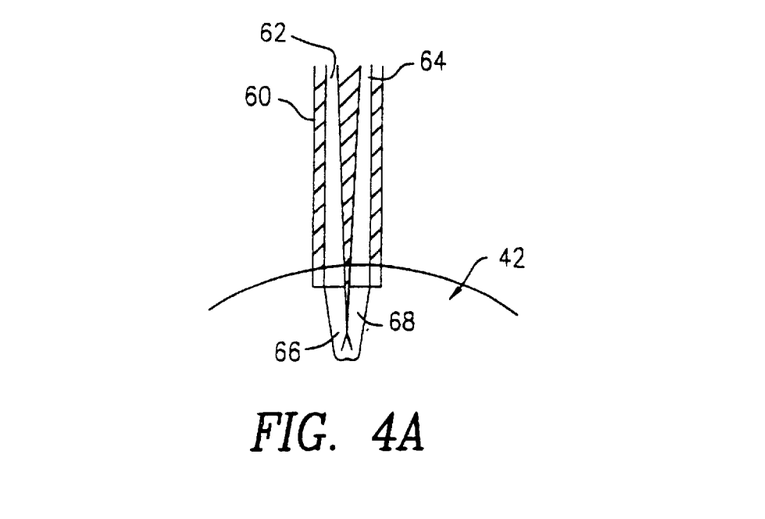
FIG. 4A shows a tool useful in the installation of the device shown in FIG. 4.
Figure 4B:
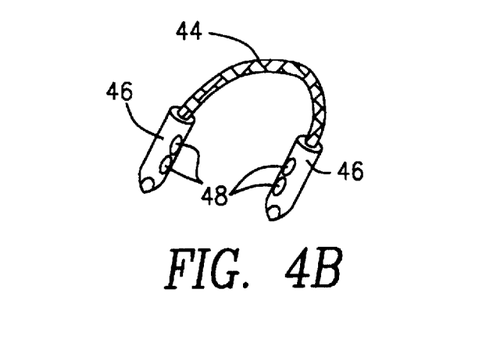
FIG. 4B is a perspective view of the device of FIG. 4.

FIGS. 4 and 4B shows the suture staple of FIGS. 2 and 3 according to the invention employing a suture 44 and sleeves 46 with openings 48 for the mixed polymer installed in harder bone.

To use the device in harder bone, a drill guide 60 shown in FIG. 4A may be provided which has two openings 62 and 64 which are not parallel. A drill is inserted through each guide 62 and 64 to form non-parallel holes 66 and 68, as shown in FIG. 4A. The suture staple is shown in FIG. 4B. The staple is then inserted into the predrilled holes in the bone. Once a suitable tension has been applied to the suture 44 for holding the tissue 40 to the bone 42, the polymer is injected into the member 46 using the tool of FIG. 1 having two injecting needles. The polymer exits from the openings 48. Once the polymer is cured, the suture staple has been secured to the tissue 42 and the tissue 40 thereby secured to the tissue 42.

One purpose of drilling the nonparallel holes is essentially to form a closed loop. That is, the distal ends of the two nonparallel guide holes interconnect, thus forming a stronger staple once the polymer cures because of the interconnection than would be formed if the two drilled holes did not connect together.

Figure 5A:
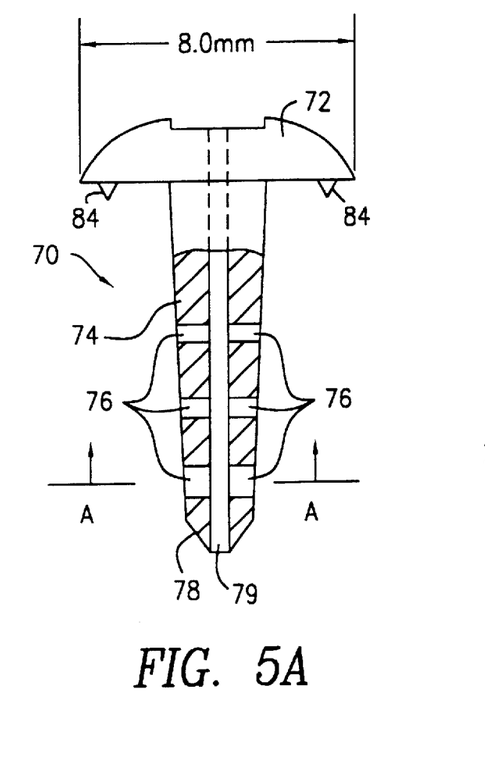
FIG. 5A is a cross-section view of an embodiment of a fastener without the installation tool.
Figure 5B:
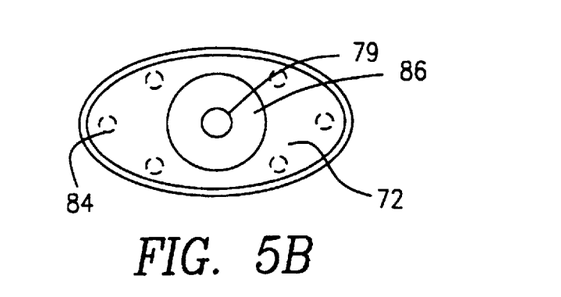
FIG. 5B is a top view of the device shown in FIG. 5A.
Figure 5C:
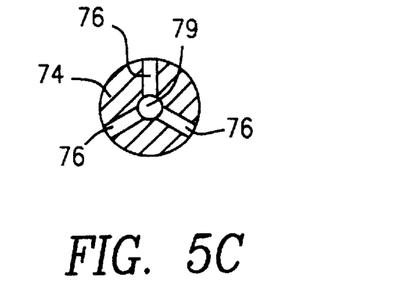
FIG. 5C is a bottom view of the device shown in FIG. 5A.
Figure 5D:
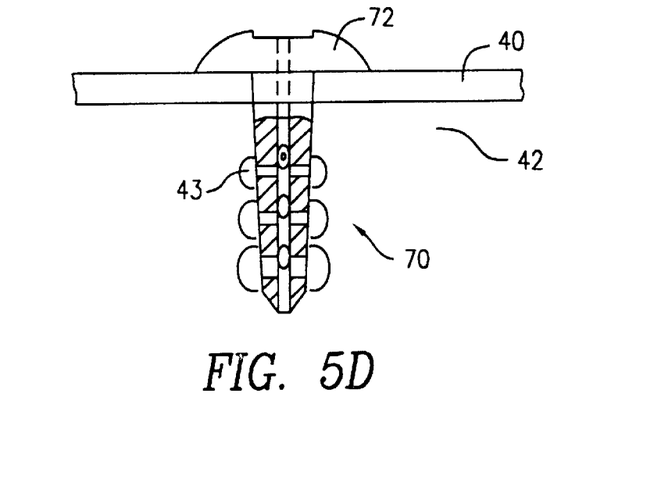
FIG. 5D is a partly cross-sectional view of the fastener of FIG. 5A securing two tissues together.

FIGS. 5A and 5B show an embodiment of a polymer anchor according to the present invention which comprises a fastener or rivet 70 having a head 72 provided with a shaft 74 and longitudinal passageway or bore 79 having exit holes 76 for dispensing a mixed polymer. The fastener can be employed, for example, to fasten a tissue such as the tissue 40 to another tissue such as the tissue 42 described previously. Preferably, the end of the fastener 78 is sharpened to facilitate insertion. FIG. 5B shows a top view and FIG. 5C shows the bottom view. The fastener 70 is also shown in FIGS. 1A 1B and 1C at the distal end of the tool. The fastener 70 can be used to secure a suture or prosthesis to tissue. For example, the needle 24A of FIGS. 7A and 7B can be used to dispense the polymer into the passageway 79 leaving a suture disposed in the passageway 79 secured to the fastener 70 by the cured polymer. Alternatively, a suture can be secured directly to the fastener 70 by being molded or otherwise fastened to the fastener 70. The fastener 70 can be used to secure first and second tissues together by passing the fastener first through one of the tissues and then into the second tissue, like for example, the tissues 40 and 42 shown in FIG. 5D. Suitable dimensions for fastener 70 may be, for example only, 15 mm in length with a shaft O.D. of 3.25 mm and an elliptical head 72 having a greater diameter of 8.0 mm, a smaller diameter of 6.0 mm, a thickness of 2.0 mm, passage 79 having a diameter of 1.75 mm and passages 76 having a diameter of 1.75 mm and spaced 3.0 mm apart. The passages may have any shape, for example, slots, without limitation.

Figure 6:
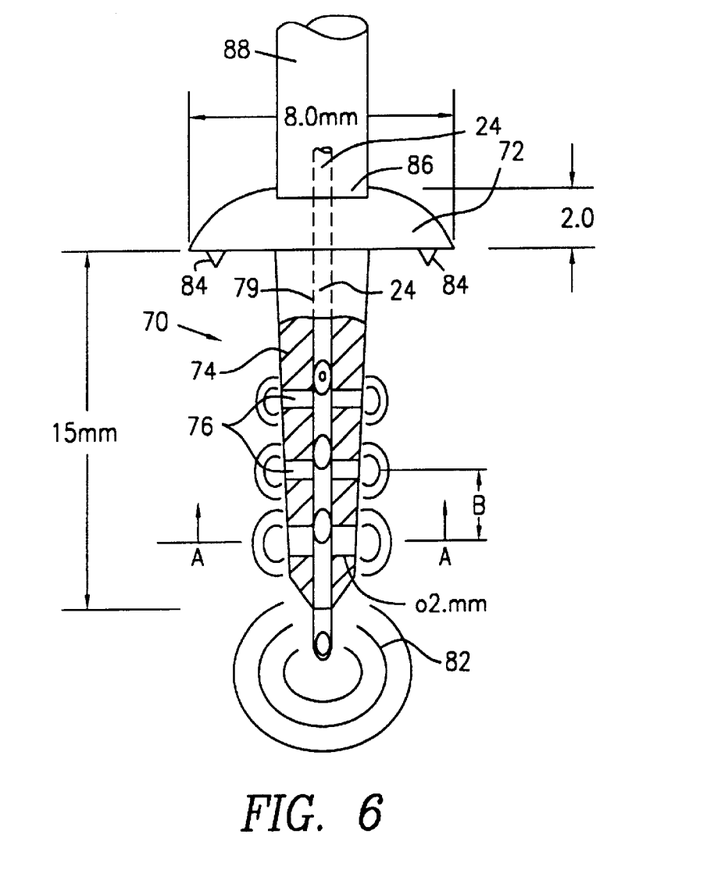
FIG. 6 is a cross-section view of the device shown in FIG. 5A after a flowable material has been delivered in and through the device.

FIG. 6 shows the fastener of FIG. 5 and how it would be used with a dispensing tool for dispensing polymer. For example, a needle such as the needle 24 is inserted through the bore 79 provided in the fastener. The needle is first inserted fully into the fastener and polymer is injected first as indicated at 82 at the distal end. The needle is then preferably drawn upwardly as the polymer is dispensed from the needle. This allows the polymer to be distributed to the respective holes 76 as the needle is being drawn upwardly, ensuring an even or a desired distribution of the polymer into the tissue and therefore securement of the fastener 70 to the tissue. The distribution need not be uniform. For example, it may be desired to have a greater distribution of polymer at the ends or in between the ends.

As shown in the drawing figures, the fastener can be provided with barbs 84 beneath the rivet head to facilitate holding of tissue onto the head. Furthermore, the shaft 74 of the fastener 70 may have screw threads, flutes, or other fixating means so that it can be screwed or otherwise fixed in the medium. The flowable curable material thus enhances the securement of the fastener 70 in the medium.

According to the invention, the head 72 of the fastener 70 may include a recessed area 86. This area may be polished for light transmission. All other surfaces of the fastener are preferably matte to reduce light loss. A fiber optic cable 88 can be coupled to the recess 86 to transmit external energy to the polymer. The polymer may, for example, rigidize or harden upon irradiation by the external energy. For example, the energy may be infrared radiation which causes the polymer to cure. Alternatively, heat energy or any other suitable energy source compatible with the curing process of the flowable material may be employed.

Alternatively, as in the prior examples, the polymer may be a two or more component polymer which cures once the two components have been mixed after an elapsed time. If the polymer cures by irradiation with externally applied energy, then it is not necessary to use a double barrelled syringe. A single barrel syringe would be all that is required.

Examples of suitable flowable materials which can be used in the invention, include, without limitation, such materials as polypropylene fumarate, polymethyl methacrylate (PMMA), and various cross linking polymers. These are merely examples which can be used in a two or more component system. Other materials can be used.

Examples of materials which can be used with single barrel delivery tools include, without limitation, a methacrylate copolymer which undergoes a phase transition when exposed to heat. By reheating this material, the material reflows, allowing for removal of the fastener. There are other materials that could be employed, including materials that flow upon cooling and harden with an increase in temperature, for example, a protein based polymer.

Although flowable curable materials may be employed such as PMMA which harden when they cure, other materials which do not harden but instead become elastic or a gel when they cure may also be employed. By "curable" herein is meant any of these materials which change state, undergo a phase transition, or harden, gel or otherwise change form, based on any process, e.g., chemical, irradiation, phase transition,etc.

Turning again to FIG. 1, if a two component polymer is used, the two components A and B in the double barreled syringe may comprise two liquids. Alternatively, the components can be powders or a liquid and a powder or combination of liquids and powders. Further, more than two components can be used, for example, three or more components, although a two component embodiment is shown in FIG. 1.

For example, if one of the components is a powder and the other a liquid, the mixing device mixes the powder with the liquid to cause the initiation of the polymerization of the mixed polymer. The advantage of using a liquid/powder system is that the two components, one being liquid and one being powder, have longer or indefinite shelf lives as compared with two liquids. Certain two component polymers which are both liquids have a shelf life so that the liquids may start to gel or polymerize by themselves prior to mixing. The present invention, using an at least two part system, one of which may comprise a powder, eliminates this problem and allows a longer or indefinite shelf life. Preferably, the fluid is polyvinylpyrrolidone (PVP) which initiates the cross-linking and the powder preferably is polypropylene fumarate (PPF). Alternatively, the two components may comprise PMMA or some other two or more component system such as calcium phosphate saline solution. The chambers for the components A and B, one of which is the powder and one of which is for the liquid, may be of different diameters depending upon the mixing ratio requirement. Further, both components may be flowable particulates.

The powder/fluid delivery system can be used both with the anchor 70, staple 41 or 31 A described herein and also as a means for delivering a bone cement or polymer to a surgical area by itself, i.e., without injection into an anchor or fastener. Accordingly, what is described herein is a method for providing a polymer which cures after mixing of the two components and delivery into the tissue.

FIGS. 7A and 7B show one example of the needle 24A and the tip of the needle 26A useful for securing a suture alone into a tissue. The suture is a form of non-flowable implant. As shown in these figures, the needle 24A has a step down inside diameter such that a knot 33 at one end of the suture strand 31 will fit into an increased diameter section 24BB at the distal tip of the hypodermic needle. See FIG. 7A. Part of the suture strand 31 will then be captured within the narrower inside diameter 24AA with the suture 31 emanating from a side slot 24CC in the hypodermic needle. See FIG. 7B.

FIG. 7C shows a modified form of the tool of FIG. 1A having two needles 24A for installing a suture staple 31 A extending between the needles. FIG. 7D shows the installed suture staple 31A securing tissue 40 to bone or other tissue 42. The injected, cured polymer is shown by the shading 43.

The polymer, once cured, secures the suture staple 31 A in position, thus securing the tissue 40 to tissue 42.

Once the suture is loaded onto a needle 24A of a double barrel syringe tool, for example, a tool as shown in FIG. 1A, the surgeon will push the needle through the soft tissue and bone and inject the flowable curable polymer. Since the inside diameter 24AA and 24BB of the hypodermic needle is larger than the diameter of the suture strand 31, the flowable polymer will flow through the hypodermic needle and out the side slots 24CC, about and above the knot 33. The polymer will flow into the cancellous bone cells to provide a barrier to the suture knot. Once the polymer has cured, the metallic hypodermic needle (or needles in the case of a suture staple) can be withdrawn leaving the suture and cured polymer to hold the soft tissue onto the bone until it is healed.

Modifications to the disclosed embodiment shown in FIGS. 7A and 7B include, but are not limited to, pushing a looped, instead of a knotted suture, through and into the tissue with a needle having a forked end, for example, and predrilling a hole into the bone before delivering the suture and the curable polymer.

Figures 8, 8A, 8B:
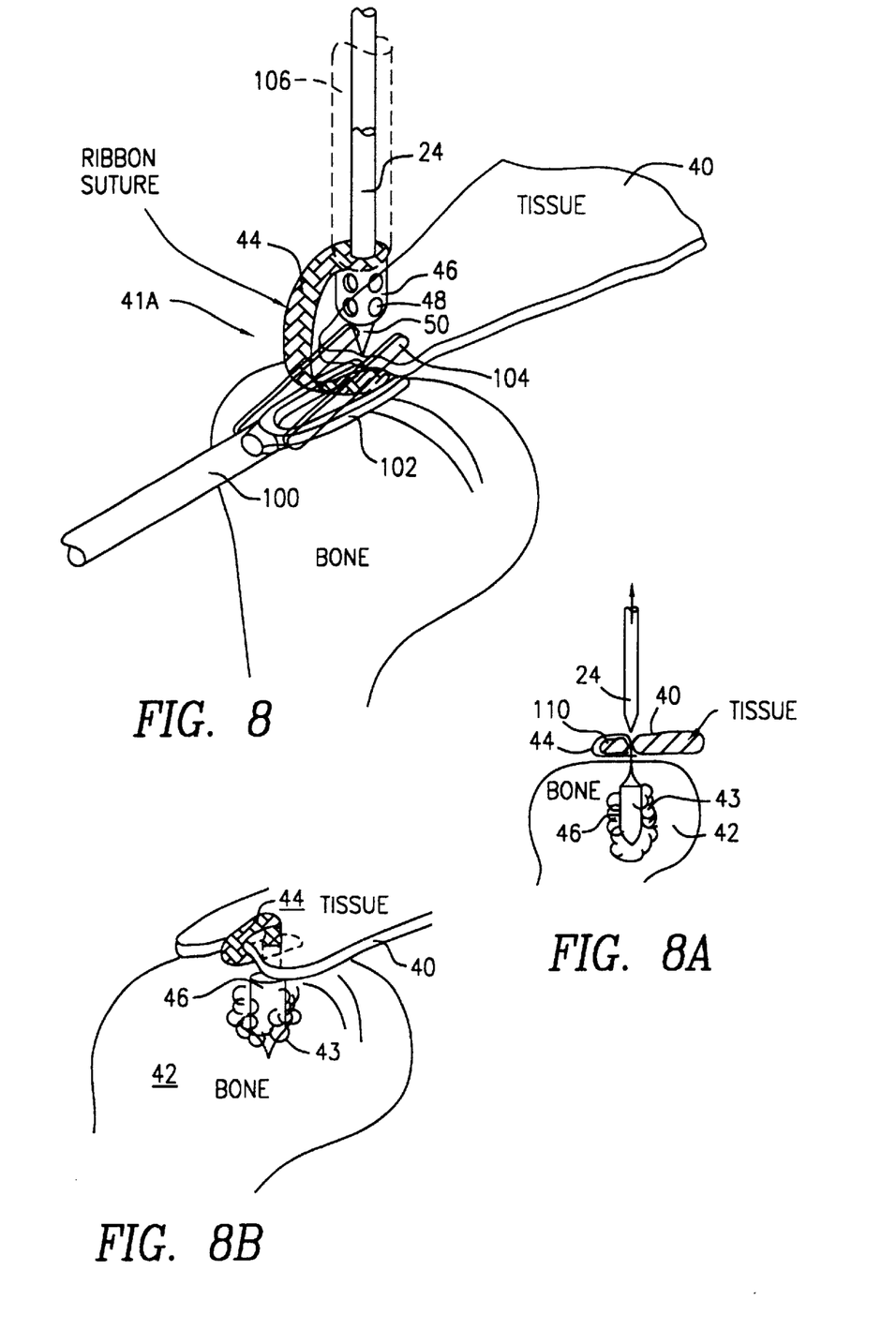
FIGS. 8, 8A, 8B and 8C show another device for fixing a tissue member first to a second tissue member according to the invention.

FIGS. 8, 8A, 8B and 8C show further embodiments of the present invention. The invention is being utilized to connect a tissue 40 to bone 42. A suture staple 41A is provided comprising a ribbon suture 44 as in the embodiment shown in FIG. 2. However, this ribbon suture 44 includes a sleeve 46 with apertures 48 and piercing tip 50 only at one end. The other end does not have a sleeve 46 or penetrating member 50. A stabilizing device 100 comprises a forked member having two forks 102 and 104, the fork 104 being pivotal with respect to the fork 102. As shown, the tissue 40 is arranged between the two forks 102 and 104. The suture ribbon 44 is also arranged beneath the tissue 40 and between the two forks. The tool 100 with the tissue 40 and free end of the suture ribbon 44 clamped between the forks 102 and 104 is then arranged above the tissue 42 in a region where the tissue 40 is to be secured to the tissue 42. A pushing tool, shown schematically at 106, is then secured to the ribbon suture 44 by engaging the sleeve 46. The pushing tool 106 includes a bore through which a needle 24 is inserted. The pushing tool is forced through the tissue 40, through the suture 44 into the bone tissue 42. Once the tissue 40 has been secured to the bone by the penetration of the tip 50 of the sleeve 46 into the bone, as shown in FIG. 8A, the tool of FIG. 1 is used to provide the curable polymer into the sleeve 46 which exits through the openings 48 in a distribution pattern 43 as shown in FIG. 8A. The tissue is thus secured as shown at 110 in FIG. 8A between the loop of the ribbon suture 44. This is' shown in cross-section in FIG. 8A and in perspective view in FIG. 8B.

Figure 8C:
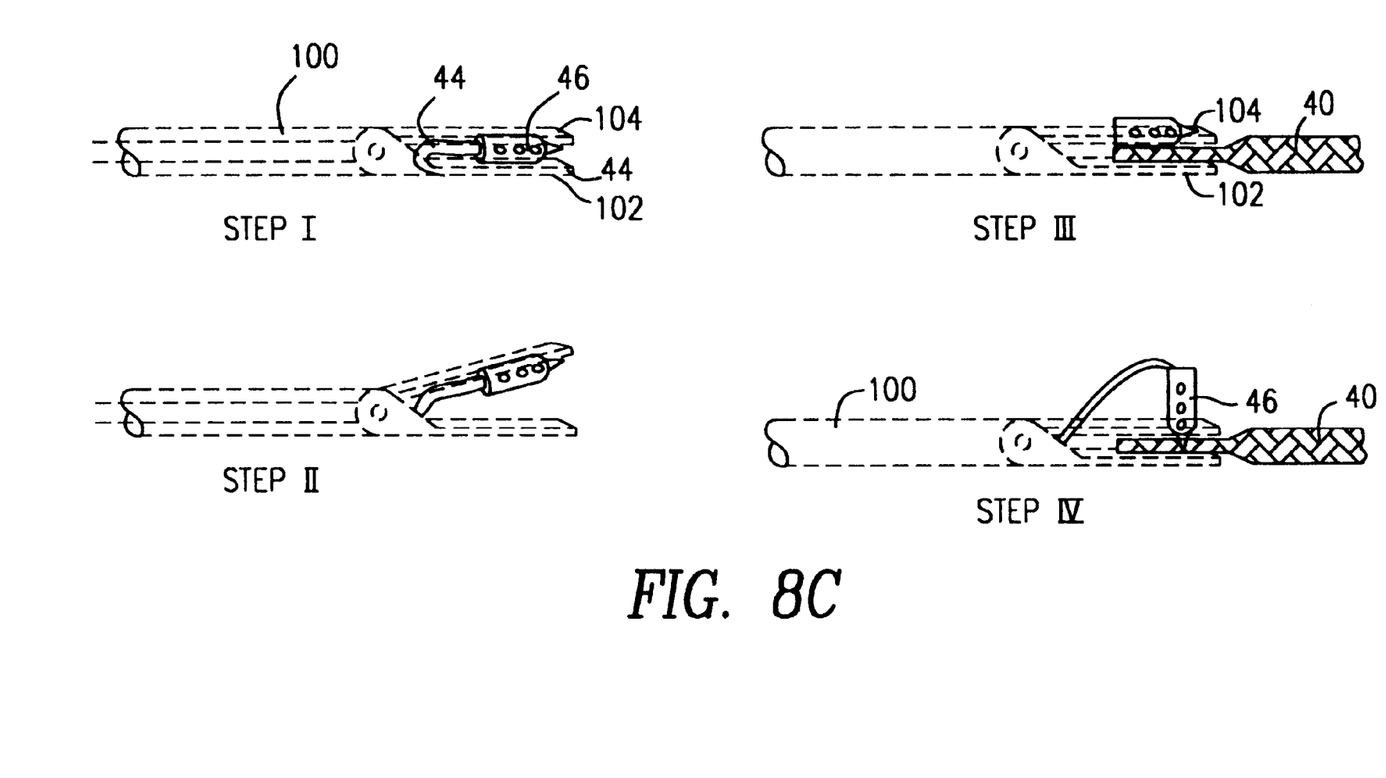

FIG. 8C shows the steps which may be employed to use the device shown in FIGS. 8, 8A and 8B. As shown in FIG. 8C, in step I, the ribbon suture 44 with the sleeve 46 is disposed along the axis of the tool 100 with the free end of the ribbon suture 44 disposed between the forks 102 and 104. The forks 102 and 104 may use spring pressure to cause a clamping action between the members 102 and 104. The forks 102 and 104 are then opened, shown at step II, and the tissue 40 is inserted therebetween. The two forks 102 and 104 are then closed, thereby securing the ribbon suture 44 and the tissue 40 therebetween. As shown in step IV, the sleeve 46 is then disposed perpendicular to the longitudinal axis of the tool 100 and the tissue 40 and the tool 106 is then used to force the sleeve 46 with its penetrating point through the tissue 40, through the free end of the ribbon suture 44 into the underlying bone 42, not shown in FIG. 8C. Then the needle 24 which is disposed in the bore of the pushing tool 106 is used to deliver the polymer to secure the sleeve in the tissue 42.

Figure 9:
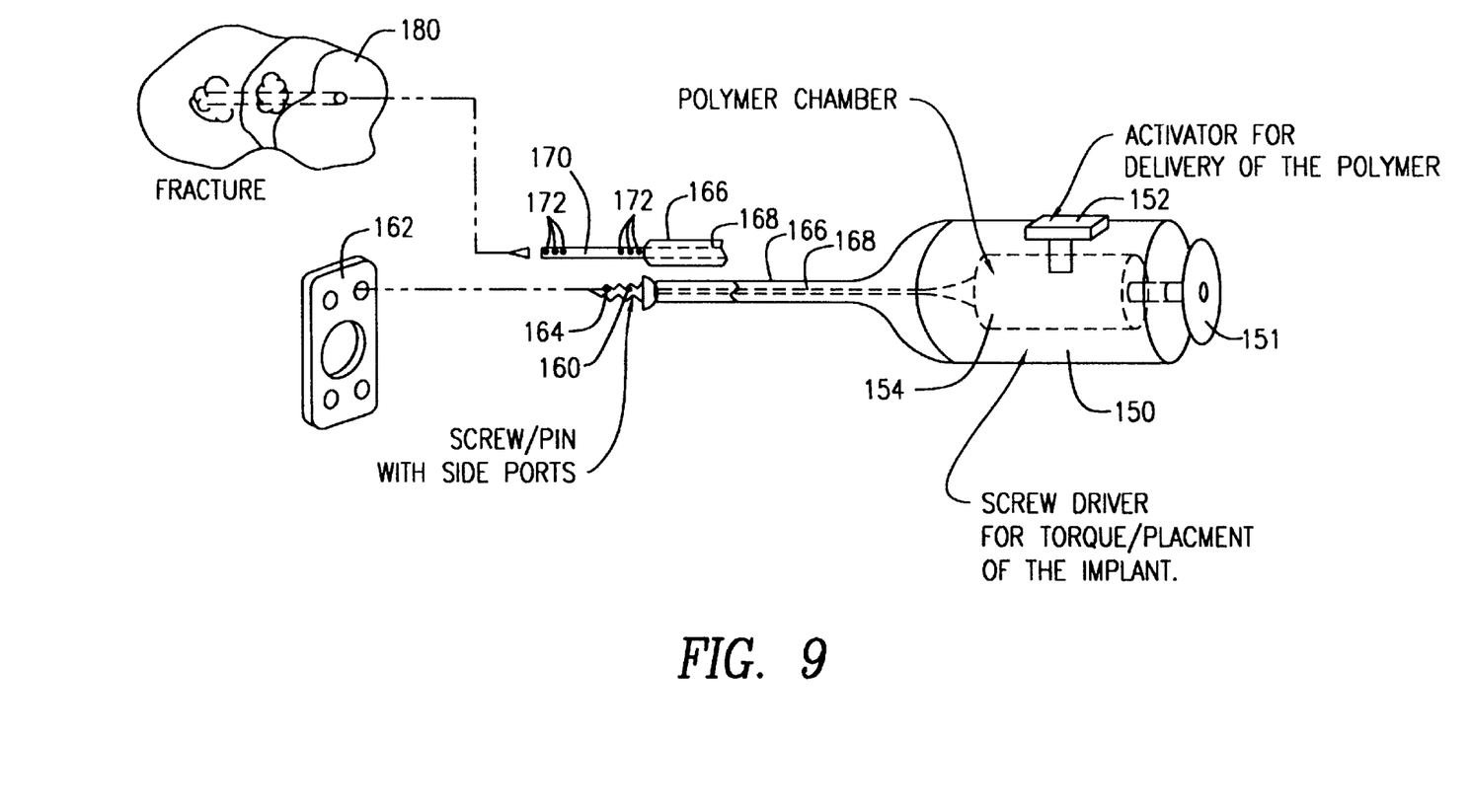
FIG. 9 shows another tool for inserting and fastening a fixation device with a flowable polymer.

FIG. 9 shows another device for implanting the fixation device and a flowable polymer with a single action. The device comprises a handle 150 having an activator for delivery of the polymer. The activator may be an activator as shown at 151 or the activator shown at 152 or some other activator. The one or two (or more) component polymer is located in a chamber 154. The handle 150 can be used to turn a screw type anchor 160 which is used to secure, for example, a plate 162, to tissue such as bone. The screw 160 has an internal longitudinal passageway which has external openings 164 for external passage of the polymer. The handle 150 includes a shaft 166 including a passageway 168 for delivery of the polymer. Utilizing the activator 151 or 152, the polymer is forced through the passageway 168 into the screw 160 and out the openings 164, once the screw has been inserted into the tissue, thereby securing the screw and for example, plate 162, to the tissue. The screw 160 may be very similar to the fastener of FIG. 5A, but provided with external screw threads on the shaft 74 of the device of FIG. 5A.

Alternatively, as shown in FIG. 9, a rod-like device 170 can be disposed at the end of the handle 150. The rod-like device 170 includes a central bore and exit holes 172 for the polymer. Such a device can be used to immobilize a fractured bone, for example, as shown at 180. The member 170 is inserted through a predrilled passage in the fractured member or is forced into the tissue, forming its opening in the tissue. The polymer is then forced through the internal bore in the rod-like member 170. The polymer exits through openings 172 to secure the rod to the fractured bone, thus immobilizing the fracture. Upon setting of the polymer, the fracture has been immobilized to allow subsequent bone growth to heal the fracture. The member 170 can have suitable flutes, serrations, etc., to aid in securement.

As shown in FIG. 9, with the screw type device, the handle 150 is used like a screw driver. The screw 160 is screwed into the tissue. If the rod 170 is used instead, the tool is used to force the rod 170 into the fracture. The fracture may be predrilled for the rod or the rod forced into the tissue without predrilling.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. A method for delivering a non-flowable implant and a flowable material into a medium with a delivery tool comprising:
   disposing a flowable material in the delivery tool;
   controlling a non-flowable implant with the delivery tool;
   inserting the non-flowable implant with the delivery tool into the medium;
   injecting the flowable material with the delivery tool into the medium so that the flowable material is injected through, above, below or around at least a portion of the non-flowable implant; and
   allowing the flowable material to change to a non-flowable state in, on or around at least a portion of the non-flowable implant to provide fixation of the implant to the medium.

2. The method of claim 1, wherein the non-flowable implant comprises a fastener.

3. The method of claim 2, wherein the fastener has a suture attached thereto.

4. The method of claim 1, wherein the non-flowable implant comprises a suture.

5. The method of claim 1 wherein the non-flowable implant comprises tissue or bone.

6. The method of claim 1, wherein the medium comprises tissue or bone.

7. The method of claim 1, wherein the step of disposing a flowable material in the delivery tool comprises disposing an at least two component flowable curable material in the delivery tool and further comprising mixing the two components to start a curing process whereby the flowable material cures after it has been delivered into the medium to secure the non-flowable implant.

8. The method of claim 1, further comprising injecting the flowable material through a portion of the delivery tool having a hollow distal end for passage of the flowable material into the medium.

9. The method of claim 1, wherein the flowable material comprises a one component flowable curable material which is curable upon exposure to an external agent.

10. The method of claim 1, wherein the flowable material comprises at least a portion that is remodelable into tissue.

11. The method of claim 1, wherein the flowable material becomes non-flowable through a phase transition.

12. The method of claim 11, wherein the flowable material which has become non-flowable can become flowable through a reverse phase transition.

13. The method of claim 9, wherein the external agent is radiation by radiant energy.

14. The method of claim 7, wherein the at least two components comprise two liquids.

15. The method of claim 7, wherein the at least two components comprise a liquid and a powder.

16. The method of claim 1, wherein the non-flowable implant comprises a fastener having a shaft, a bore extending through the shaft, and further comprising providing a needle having a distal opening in the bore, and injecting the flowable material through the needle into the bore, the fastener having at least one opening for communication of the flowable material between the bore and the medium.

17. The method of claim 16, wherein the fastener has a plurality of openings communicating between the bore and the medium, and further comprising injecting the flowable material through ones of the plurality of openings.

18. The method of claim 17, further comprising injecting the flowable material through ones of the plurality of openings to achieve a desired distribution of the flowable material in the medium.

19. The method of claim 18, further comprising moving the needle relative to the bore of the fastener to achieve the desired distribution.

20. The method of claim 1, further comprising disposing the flowable material in at least one chamber of the delivery tool and moving a plunger in the chamber to inject the flowable material into the medium.

21. The method of claim 19, further wherein the flowable material is an at least two component material that is mixed to cause it to cure and further comprising forcing the at least two components into a mixing chamber of the delivery tool to mix the two components prior to injecting the flowable material into the medium.

22. The method of claim 1, further comprising generating a signal to indicate when the flowable material has become non-flowable to allow retraction of the delivery tool.

23. The method of claim 1, further where the medium comprises first and second members and further wherein the non-flowable implant comprises a staple device for attaching the first member to the second member and further comprising injecting the flowable material into two legs of the staple device to secure each of the two legs in the medium, with the two legs penetrating through the first member into the second member to secure the first member to the second member.

24. The method of claim 1, further comprising providing a penetrating distal end on the non-flowable implant and forcing said non-flowable implant into the medium with the delivery tool.

25. The method of claim 1, further comprising using a distal end of the delivery tool to penetrate into the medium.

26. The method of claim 1, further comprising drilling a hole in the medium and inserting the non-flowable implant in the hole.

27. The method of claim 26, further comprising drilling two holes in the medium and wherein the non-flowable implant comprises a staple device having two legs, and inserting the two legs in the respective holes.

28. The method of claim 27, wherein the step of drilling comprises drilling two non-parallel holes in the medium.

29. The method of claim 28, wherein the step of drilling two non-parallel holes comprises drilling the holes so that distal ends thereof interconnect and the step of injecting the flowable material comprises injecting the flowable material so that the flowable material in each hole contacts the flowable material in the other hole.

30. The method of claim 1, wherein a distal end of the delivery tool comprises a surgical needle having an internal bore for the flowable material, and further comprising attaching a suture to a distal portion of the needle, and injecting the flowable material through the needle around the suture in the medium, and withdrawing the needle, leaving the suture secured by the flowable material that has become non-flowable in the medium.

31. The method of claim 30, further comprising providing said internal bore of the needle for the flowable material having an increased diameter portion at the distal end thereof, whereby a knot of the suture can be disposed in the increased diameter portion.

32. The method of claim 31, further comprising providing a longitudinally extending slot in the needle communicating with the needle bore at the distal end, thereby to allow the needle to be removed from the suture before or after when the flowable material has become non-flowable around the suture.

33. The method of claim 30, further comprising providing two needles on the delivery tool, with a suture attached between the two needles for use as a suture staple in the medium.

34. The method of claim 1, further comprising providing at least one sleeve attached to a flexible member, using the delivery tool to insert the sleeve in the medium, and injecting the flowable material into the sleeve using the delivery tool, the sleeve having at least one opening communicating with the medium, the step of injecting including forcing the flowable material through the at least one opening into the medium and allowing the flowable material to become non-flowable to secure the sleeve in the medium.

35. The method of claim 34, further comprising providing a sleeve on two ends of a length of the flexible member, inserting the sleeve on each end into the medium with the delivery tool and injecting the flowable material with the delivery tool into the two sleeves to secure the sleeves to the medium.

36. The method of claim 30, wherein any component of the non-flowable implant and flowable material is at least one of biodegradable, bioabsorbable, remodelable, and permanent.

37. The method of claim 34, wherein the medium comprises first and second members, further comprising disposing the sleeve through the first member, through the flexible member and then into the second member to form a loop around a portion of the first member thereby to secure the first member to the second member.

38. The method of claim 1, wherein the delivery tool comprises a rotatable instrument, and further comprising providing the non-flowable implant with a screw thread to enable threading of the non-flowable implant into the medium by rotating the delivery tool.

39. The method of claim 1, wherein the delivery tool comprises a device for applying an axial force to the non-flowable implant to cause the non-flowable implant to be inserted into the medium.

40. The method of claim 39, wherein the non-flowable implant is driven into the medium by the delivery tool without predrilling a hole.

41. The method of claim 39, further comprising predrilling a hole in the medium for the non-flowable implant.

42. A tool for delivering a non-flowable implant and a flowable material into a medium comprising:

a chamber for the flowable material;

a longitudinally extending member having a bore;

a holder for the non-flowable implant disposed at a distal portion of the longitudinally extending member;

the bore being provided for delivering the flowable material into the medium so that the flowable material is injected through, above, below or around at least a portion of the non-flowable implant; and wherein the flowable material changes to a non-flowable state in, on or around at least a portion of the non-flowable implant to provide fixation of the implant to the medium.

43. The tool of claim 42, wherein the non-flowable implant comprises a fastener.

44. The tool of claim 43, wherein the fastener has a suture attached thereto.

45. The tool of claim 42, wherein the non-flowable implant comprises a suture.

46. The tool of claim 42, wherein the non-flowable implant comprises tissue or bone.

47. The tool of claim 42, wherein the medium comprises tissue or bone.

48. The tool of claim 42, wherein the flowable material comprises an at least two component flowable curable material and further comprising a mixing chamber for mixing the two components to start a curing process whereby the flowable material cures after it has been delivered into the medium to secure the non-flowable implant in the medium.

49. The tool of claim 42, further wherein the delivery tool has a hollow distal end for passage of the flowable material into the medium.

50. The tool of claim 42, wherein the flowable material comprises a one component flowable curable material which is curable upon exposure to an external agent.

51. The tool of claim 42, wherein the flowable material comprises at least a portion that is remodelable into tissue.

52. The tool of claim 42, wherein the flowable material becomes non-flowable through a phase transition.

53. The method of claim 52, wherein the flowable material which has become non-flowable can become flowable through a reverse phase transition.

54. The tool of claim 50, wherein the external agent is radiant energy.

55. The tool of claim 48, wherein the at least two components comprise two liquids.

56. The tool of claim 48, wherein the at least two components comprises a liquid and a powder.

57. The tool of claim 42, wherein the non-flowable implant comprises a fastener having a shaft, a bore extending through the shaft, and further wherein the longitudinally extending member comprises a needle received in the bore of the shaft and having an internal bore, the needle bore having a distal opening, whereby the flowable material is injected through the needle into the bore of the fastener, the fastener having at least one opening for communication of the flowable material between the bore of the shaft and the medium.

58. The tool of claim 57, wherein the fastener has a plurality of openings communicating between the shaft bore and the medium, and further wherein the flowable material is injected through ones of the plurality of openings.

59. The tool of claim 58, further wherein the flowable material is injected through ones of the plurality of openings to achieve a desired distribution of the flowable material in the medium.

60. The tool of claim 59, further wherein the needle is movable relative to the bore of the fastener to achieve the desired distribution.

61. The tool of claim 42, further comprising at least one chamber for the flowable material and a plunger in the chamber to inject the flowable material into the medium.

62. The tool of claim 61, further wherein the flowable material is an at least two component material that is mixed to cause it to cure and further comprising a mixing chamber to mix the two components prior to injecting the flowable material into the medium.

63. The tool of claim 42, further comprising a signal generator to indicate when the flowable material has become non-flowable to allow retraction of the delivery tool from the medium.

64. The tool of claim 42, further where the medium comprises first and second members and further wherein the non-flowable implant comprises a staple device for attaching the first member to the second member and further wherein the staple device has two legs for insertion into the medium, with the two legs penetrating through the first member into the second member to secure the first member to the second member.

65. The tool of claim 42, further comprising a penetrating distal end on the non-flowable implant whereby the implant can be forced into the medium with the delivery tool.

66. The tool of claim 42, further comprising a distal end of the delivery tool for penetrating into the medium.

67. The tool of claim 42, further comprising means for drilling a hole in the medium prior to insertion of the non-flowable implant in the hole.

68. The tool of claim 67, further comprising a guide for drilling two holes in the medium and wherein the non-flowable implant comprises a staple device having two legs for insertion in the respective holes.

69. The tool of claim 68, wherein the guide comprises a drill guide for drilling two non-parallel holes in the medium.

70. The tool of claim 69, wherein the guide for drilling two non-parallel holes comprises a guide arranged for drilling the holes so that distal ends thereof interconnect whereby the flowable material injected in each hole contacts the flowable material in the other hole.

71. The tool of claim 42, further comprising a suture attached to the distal end of the needle, whereby the flowable material can be injected through the needle around the suture in the medium, the needle being withdrawn, leaving the suture secured by the flowable material that has become non-flowable in the medium.

72. The tool of claim 71, further wherein said needle has an internal bore for the flowable material having an increased diameter portion at the distal end thereof, whereby a knot of the suture can be disposed in the increased diameter portion.

73. The tool of claim 72, further comprising a longitudinally extending slot in the needle communicating with the needle bore at the distal end, thereby to allow the needle to be removed from the suture when the flowable material has become non-flowable around the suture.

74. The tool of claim 71, further comprising two needles on the delivery tool, with a suture attached between the two needles for use as a suture staple in the medium.

75. The tool of claim 42, further comprising at least one sleeve attached to a flexible member, the sleeve being insertable into the medium, the sleeve having at least one opening communicating with the medium, whereby the flowable material is injectable through the at least one opening into the medium to thereby secure the sleeve in the medium once the flowable material has become non-flowable.

76. The tool of claim 75, further comprising a sleeve on each of two ends of a length of the flexible member for insertion into the medium whereby the flowable material can be injected into the two sleeves to secure the sleeves to the medium as a staple.

77. The tool of claim 75, wherein any component of the non-flowable implant and flowable material is at least one of biodegradable, bioabsorbable, remodelable and permanent.

78. The tool of claim 75, wherein the medium comprises a first member and a second member, further comprising means for disposing the sleeve through the first member, through the flexible member and then into the second member to form a loop around a portion of the first member thereby to secure the first member to the second member.

79. The tool of claim 42, wherein the delivery tool comprises a rotatable instrument, and further wherein the non-flowable implant has a screw thread to enable threading of the non-flowable implant into the medium by rotating the delivery tool.

80. The tool of claim 42, wherein the delivery tool comprises a device for applying an axial force to the non-flowable implant to cause the non-flowable implant to be inserted into the medium.

81. The tool of claim 80, wherein the non-flowable implant is driven into the medium by the delivery tool without predrilling a hole.

82. The tool of claim 80, further comprising means for predrilling a hole in the medium for the non-flowable implant.

83. The tool of claim 42, further comprising a proximal handle that functions to allow insertion of the implant and injection of the flowable material into the medium.

84. The tool of claim 83, wherein the handle includes a trigger for actuating movement of the flowable material from the chamber into the medium for securing the implant in the medium.

85. A tool for installing a non-flowable implant and a flowable material for securing the implant in a medium, the tool comprising:

a hollow distal longitudinal section having at least a portion in contact with at least a portion of the implant;

the distal longitudinal section of the tool being capable of controlling the implant and delivering the flowable material into the medium; and the distal longitudinal section being connected to a proximal handle that functions to allow insertion of the implant and injection of the flowable material into the medium.

86. A method for installing a non-flowable implant and a flowable material for securing the implant in a medium, the method comprising:

using an installation tool having a hollow distal longitudinal section with at least a portion in contact with at least a portion of the implant;

controlling the implant and delivering the flowable material into the medium with the distal longitudinal section; and manipulating a proximal handle of the tool to both insert the implant and inject the flowable material into the medium thereby securing the implant in the medium.

87. A surgical implant comprising:

a length of a flexible material;

at least one sleeve having at least one axial hole therethrough and at least one transverse opening communicating with the axial hole;

one end of the flexible material being connected to the sleeve;

the sleeve being adapted to be received in a medium for securement in the medium, the sleeve being adapted to receive a flowable curable material that is injected through the axial hole and through the transverse opening to contact the medium thereby to secure the sleeve in the medium.

88. The implant of claim 87, further comprising a plurality of transverse openings communicating with the axial hole.

89. The implant of claim 87, wherein the flexible material comprises suture.

90. The implant of claim 87, wherein the axial hole is adapted to receive a device for injecting the flowable curable material.

91. The implant of claim 87, further comprising a second sleeve attached to a second end of the flexible material, whereby the implant functions as a surgical staple.

92. The implant of claim 87, wherein any component of the implant is at least one of biodegradable, bioabsorbable, remodelable and permanent.

93. The implant of claim 87, further comprising a penetrating end at a distal portion of the sleeve for penetration into the medium.

94. The implant of claim 90, wherein the injecting device comprises a needle having an internal bore and an opening at a distal end thereof for injecting the flowable curable material.

95. The implant of claim 94, wherein the needle is received in the axial hole and is movable in the axial hole to effect a desired distribution of the flowable material in the medium.

96. A surgical implant comprising:

a fastener having a shank, the shank having an axial opening therein and at least one transverse opening communicating with the axial opening and an exterior of the shank; and a flowable curable material received in the axial opening and through the transverse opening for contacting at least a portion of the exterior of the shank for securing the fastener to a medium in which the fastener is inserted; further comprising a suture attached to the fastener.

97. The implant of claim 96, wherein the shank has a plurality of transverse openings.

98. The implant of claim 97 wherein the axial opening is adapted to receive a needle of a tool for injecting the flowable curable material into the implant through the axial hole.

99. The implant of claim 98, wherein the needle is movable in the axial hole for effecting a desired distribution of the flowable curable material in the medium.

100. The implant of claim 96, further wherein the implant is adapted to receive radiant energy for curing the flowable curable material.

101. The implant of claim 96, wherein the shank has an external screw thread.

102. The implant of claim 96 further comprising a head at one end of the shank.

103. A surgical staple device for stapling into a medium, the staple device comprising:

two sleeves;

a bridge extending between the sleeves whereby the sleeves can be disposed substantially perpendicularly to the bridge;

the sleeves having an axial hole therethrough for a flowable curable material, the sleeves each having at least one transverse opening extending between the axial hole and an external surface of the sleeve for communicating the flowable curable material between the axial hole and the medium for scuring the sleeve to the medium.

104. The surgical staple of claim 103 wherein the bridge is flexible.

105. The surgical staple of claim 104, wherein the bridge comprises a suture.

106. The surgical staple of claim 103, further comprising a flowable curable material contacting at least a portion of the sleeve to secure the staple in the medium.

107. The surgical staple of claim 103, further comprising a plurality of transverse openings in the sleeve.

108. The surgical staple of claim 103, further comprising a penetrating point at a distal end of each sleeve.

109. The surgical staple of claim 103, wherein the axial hole is adapted to receive a device for distributing the flowable curable material to the medium.

110. A surgical implant comprising:

a length of suture having ends for disposition in two respective holes in a medium to secure a first tissue to the medium, the two ends being disposed through respective holes in the first tissue and into respective aligned holes in the medium; and a flowable curable material disposed about at least a portion of each of the ends in the holes in the medium, the flowable curable material being adapted to secure the ends to the medium.

\* \* \* \* \*